United States Patent
Dolphin et al.

(10) Patent No.: US 6,331,235 B1
(45) Date of Patent: Dec. 18, 2001

(54) CHIRAL SEPARATION OF BENZOPORPHYRIN DERIVATIVE MONO-AND DI-ACIDS BY LASER-INDUCED FLUORESCENCE CAPILLARY ELECTROPHORESIS

(75) Inventors: David Dolphin; Xuejun Peng; Ethan D. Sternberg, all of Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/321,893

(22) Filed: May 28, 1999

Related U.S. Application Data
(60) Provisional application No. 60/111,955, filed on Dec. 11, 1998.

(51) Int. Cl.$^7$ .................................................. G02N 27/26
(52) U.S. Cl. ........................................................... 204/451
(58) Field of Search ...................................... 204/450, 451

(56) References Cited

U.S. PATENT DOCUMENTS
5,171,749    12/1992    Levy et al. ............................ 514/410

OTHER PUBLICATIONS

Dixon et al. ("Capillary electrophoretic separation of cationic porphyrins", Journal of Liquid Chromatography A, 802(Apr. 1998), 367–380.*

CAPLUS abstract of Wu et al. ("Separation of porphyrins using a .gamma.–cyclodextrin stationary phase", J. Liq. Chromatogr. (Month unknown 1994), 17(5), 1111–24.*

CAPLUS abstract of Fanali et al. ("The utility of cyclodextrins in capillary electrophoresis", J. Capillary Electrophor. (Month unknown 1994), 1(10, 72–8).*

CAPLUS abstract of Armstrong et al. (Derivatized cyclodextrins immobilized on fused–silica capillaries for eantiomeric separations via capillary electrophoresis, gas chromatograph, or supercritical fluid chromatography, Anal. Chem. (Month unknown 1993), 65(8), (114–17).*

Wu et al. ("Recent developments in Porphyrin Separations using Capillary Electrophoresis with Native Fluorescence Detection", Journal of Liquid Chromatography, 1799), 1917–1927 (1994)).*

Yao et al. ("Optimization of separation of porphyrins by micellar electrokinetic chromatography using the overlapping resolution mapping scheme", Journal of Chromatography, 637(1993) 195–200).*

Chan et al. ("Capillary electrophoresis analysis of polyhaematoporphyrin, a photosensitizer used in photodynamic therapy", Journal of Chromatography, 636 (1993) 171–178).*

Jamieson et al. (1990). *Leukemia Research* 14(3):209–219, Month Unknown.

Aveline, B. M. et al., The Effects Of Aggregation, Protein Binding And Cellular Incorporation On The Photophysical Properties Of Benzoporphyrin Derivative Monoacid Ring A (BPDMA), J. Photochem. Photobiol. B Biology (1995), Month unknown 30:161–69.

(List continued on next page.)

*Primary Examiner*—Jill Warden
*Assistant Examiner*—Alex Noguerola

(57) ABSTRACT

A method for the separation of benzoporphyrin derivative mono and diacid (BPD-MA, BPD-DA) enantiomers by Laser-Induced Fluorescence Capillary Electrophoresis has been developed. The limits of detection are $2.06 \times 10^{-6}$ M, and the relative standard deviation for the separation was 2.90% to 4.64%. The BPD enantiomers can be quantitatively determined in the range of $10^{-2}$ to $10^{-5}$ mg mL$^{-1}$. In comparison with HPLC, CE has better resolution and efficiency. This separation method was successfully applied to the BPD enantiomers obtained from a matrix of bovine serum and from liposomally formulated material as well as from studies with rat, dog and human microsomes.

21 Claims, 10 Drawing Sheets-

OTHER PUBLICATIONS

Beukeveld, G. J. J. et al., Determination Of Porphyrins In Bile Using High Performance Liquid Chromatography And Some Clinical Applications, Eur. J. Clin. Chem. Clin. Biochem. (1994), Month unknown 32:153–59.

Böeseken, J., The Use Of Boric Acid For The Determination Of The Configuration Of Carbohydrates, Adv. Carbohydr. Chem. (1949), Month unknown 32:153–59.

Bowser, M. T. et al., Development And Application Of A Nonaqueous Capillary Electrophoresis System For The Analysis Of Porphyrins And Their Oligomers (Photofrin), Analytical Biochemistry (1996), Month unknown 241:143–50.

Bowser, M. T. et al., Quantitative Description Of Migration Behavior Of Porphyrins Based On The Dynamic Complexation Model In A Nonaqueous Capillary Electrophoresis System, Electrophoresis (1997) Month unknown 18:82–91.

Consden, R. et al., Ionophoresis Of Sugars On Paper And Some Applications To The Analysis Of Protein Polysaccharide Complexes, Nature (1952), Month unknown 169:783–85.

Delaney, T. F. et al., Photodynamic Therapy Of Cancer, Comprehensive Therapy (1988), Month unknown 14(5):43–55.

Hjertén, S., Free Zone Electrophoresis, Chromatog. Rev. (1967), Month unknown 9:122–219.

Ho, J. W. et al., Effects Of Injection Solvents On The Separation Of Porphyrin And Metalloporphyrin In Reversed–Phase Liquid Chromatography, J. Liq. Chromatogr. (1994), Month unknown 17(3):549–58.

Hoffstetter–Kuhn, S. et al., Influence Of Borate Complexation On The Electrophoretic Behavior Of Carbohydrates In Capillary Elctrophoresis, Anal. Chem. (1991), Month unknown 63:1541–47.

Honda, S. et al., Simultaneous Determination Of Reducing Monosaccharides By Capillary Zone Electrophoresis As The Borate Complexes Of N–2–Pyridylglycamines, Analytical Biochemistry (1989) 176:72–77, month unknown.

Honda, S. et al., Analysis Of The Oligosaccharides In Ovalbumin By High–Performance Capillary Electrophoresis, Analytical Biochemistry (1990) 191:228–34, month unknown.

Jamieson, C. H. M. et al., Preferential Uptake Of Benzoporphyrin Derivative By Leukemic Versus Normal Cells, Leukemia Research (1990) 14(3):209–19.

Jorgenson, J. W. et al., Free Zone Electrophoresis In Glass Capillaries, Clin. Chem. (1981) 27(9):1551–53 month unknown.

Kimmett, S. M. et al., Evidence For The Stereoselective Inhibition Of Chick Embryo Hepatic Ferrochelatase By N–Alkylated Porphyrins. II, Molecular Pharmacology (1992) 42:307–10 month unknown.

Landers, J. P. et al., Separation Of Boron–Complexed Diol Compounds Using High–Performance Capillary Electrophoresis, Anal. Chem. (1992) 64:2846–51 Nov.

Lim, C. K. et al., High–Performance Liquid Chromatography Of Porphyrins, J. Chromatogr. (1988) 429:123–53 month unknown.

Liu, X. et al., Capillary Electrophoresis Enzyme Immunoassay For Digoxin In Human Serum, Anal. Chem. (1995) 67:3211–18 Sep.

Miller, H. et al., Photodynamic Therapy Of Subretinal Neovascularization In The Monkey Eye, Arch. Opthalmol. (1993) 111:855–60 Jun.

Morin, P. et al., Borate Complexation Of Flavonoid–O–Glycosides In Capillary Electrophoresis, J. Chromatogr. (1993) 628:161–69 month unknown.

Neyndorff, H. C. et al., Development Of A Model To Demonstrate Photosensitizer–mediated Viral Inactivation In Blood, Transfusion (1990) 30(6):485–90.

Owens, J. W. et al., Chromatographic Analysis Of Photodynamically Significant Porphyrin Dimers And Trimers, J. Chromatogr. B (1996) 682:327–36 Jul.

Peng, X. et al., Quantitative Description Of Analyte Migration Behavior Based On Dynamic Complexation In Capillary Electrophoresis With One Or More Additives, Electrophoresis (1997) 18:706–16 month unknown.

Penn, S. G. et al., Capillary Electrophoresis With Chiral Selectors: Optimization Of Separation And Determination Of Thermodynamic Parameters For Binding Of Tioconazole Enantiomers To Cyclodextrins, Anal. Chem. (1994) 66:2866–73 month unknown.

Pietta, P. et al., Influence Of Structure On The Behavior Of Flavonoids In Capillary Electrphoresis, Electrophoresis (1994) 15:1326–31.

Richter, A. M. et al., Biodistribution Of Tritated Benzoporphyrin Derivative ($^3$ H–BPD–MA), A New Potent Photosensitizer, In Normal and Tumor–Bearing Mice, J. Photochem. Photobiol. B Biology (1990) 5:231–44 month unknown.

Richter, A. M. et al., Photosensitizing Efficiency Of Two Regioisomers Of The Benzoporphyrin Derivatives Monoacid Ring A (BPD–MA), Biochemical Pharmacology (1992) 43(11):2349–58 month unknown.

Richter, A. M. et al., Preliminary Studies on a More Effective Phototoxic Agent Than Hematoporphyrin, J. Natl. Can. Inst. (1987) 79(6):1327–32 month unknown.

Richter, A. M. et al., Characterization Of Benzoporphyrin Derivative, A New Photosensitizer, Proceedings SPIE, The International Society for Optical Engineering, Boston, MA (1988) 997:132–38 month unknown.

Richter, A. M. et al., Photosensitising Potency Of Structural Analogues Of Benzoporphyrin Derivative (BPD) In A Mouse Tumour Model, Br. J. Cancer (1991) 63:87–93 month unknown.

Sato, H. et al., Simultaneous Separation And Quantification Of Free And Metal–Chelated Protoporphyrins In Blood By Three–Dimensional HPLC, Clin. Chem. (1994)month unknown 40(7):1239–44.

Sternberg, E. et al., Pyrrolic Photosensitizers, Current Medicinal Chemistry (1996) 3:239–72 month unknown.

Udagawa, M. et al., Determination Of Coproporphyrin I And III Isomers By High–Performance Liquid Chromatography, J. Chromatogr. (1982) 233:338–42 month unknown.

Walker, C. J. et al., The Magnesium—Protoporphyrin IX (Oxidative) Cyclase System, Biochem. J. (1988) 255:685–92, Month unknown.

Wallingford, R. A. et al., Retention Of Ionic And NOn–Ionic Catechols In Capillary Zone Electrophoresis With Micellar Solutions, J. Chromatogr. (1988) 441:299–309, Month unknown.

Wan, J. R. et al., High Performance Liquid Chromatography Separation And Analysis Of Metallotetra (Pentafluorophenyl) Porpholactone, J. Liq. Chromatogr. (1994), Month unknown, 17(9):2045–56.

Weinberger, R. et al., Capillary Electrophoresis Of Urinary Porphyrins With Absorbance And Fluorescence Detection, J. Chromatogr. (1990) 516:271–85, Month unknown.

Woodburn, K. W. et al., Evaluation Of Tumor And Tissue Distribution Of Porphyrins For Use In Photodynamic Therapy, Br. J. Cancer (1992) 65:321–28.

Yao, Y. J. et al., Determiantion Of Erythrocyte Porphyrins By Epi–Illumination Fluorescence Microscope With Capillary Electrophoresis, J. Liq. Chrom. & Rel. Technol. (1996) 19(1):1–15, Month unknown.

* cited by examiner

BPDMA (Ia-1)

BPDMA (Ia-2)

BPDMA (Ib-1)

BPDMA (Ib-2)

BPDDA (II-1)

BPDDA (II-2)

VII

VIII

IX

CHIRAL SEPARATION OF BENZOPORPHYRIN DERIVATIVE MONO-AND DI-ACIDS BY LASER-INDUCED FLUORESCENCE CAPILLARY ELECTROPHORESIS

RELATED APPLICATIONS

The present application claims the benefit of U.S. Provisional Application 60/111,955, filed Dec. 11, 1998, which is hereby incorporated by reference in its entirety, as if fully set forth.

FIELD OF THE INVENTION

The invention relates to the use of capillary electrophoresis separation, as well as laser-induced fluorescence to aid in detection, of benzoporphyrin derivative (BPD) stereoisomers. These separation methods permit all four enantiomers of BPD-MA and the two of BPD-DA to be completely separated with baseline separation with high resolution and efficiency. The use of laser-induced fluorescence detection greatly improves the analytical sensitivity and selectivity of CE of BPDs. The invention is well suited as a rapid and reliable method for the separation of BPD monoacid and diacid enantiomers in a preparative or analytical application. Of particular utility is the potential for use as an analytical method with clinical samples.

DESCRIPTION OF THE RELATED ART

Photodynamic therapy (PDT) is based on the observation that some photosensitizers accumulate somewhat selectivity in tumor tissue where they can be activated by light at wave-lengths in the visible region. The photosensitizers absorb photons of visible light and use the absorbed energy to generate singlet oxygen, which is considered responsible for most of the damage leading to tumor cell death and tumor ablation (Delaney et al. (1988)). A number of photosensitizers are currently under investigation including chlorins, purpurins, phthalocyanines, and benzoporphyrin derivatives, especially benzoporphyrin derivative monoacid ring A (BPD-MA) and Verteporfin (Sternberg et al. (1996)).

BPD-MA is a novel second-generation photosensitizer for PDT which exhibits lower skin phototoxicity than Photofrin (Richter et al. (1987)) which has already been approved by Health Boards around the world. BPD-MA has been shown to be effective for the treatment of cutaneous lesions; as a promising agent for bone marrow purging and for the treatment of leukemia (Jamieson et al. (1990)), as an antiviral agent for decontamination of blood and blood products (Neyndorff et al. (1990)) and most recently for the treatment of age related macular degeneration of the eye (Miller et al. (1993)).

The importance of determining the stereoisomeric or chiral composition of chemical compounds, especially those of pharmaceutical importance, cannot be overemphasized. Nearly 60% of the most frequently prescribed drugs in the United States possess one or more asymmetric centers in the drug molecule. The physiological effects of enantiomers of these racemic drugs have not always been examined. To ensure the safety and efficacy of currently used and newly developed drugs, it is important to isolate the enantiomers and to examine each one separately. Accurate assessment of enantiomeric purity of substances is critical to investigate their toxicological and pharmacological effects and to study pharmocokinetic profiles.

Traditionally, high-performance liquid chromatography (HPLC) has been the most commonly used method for the separation of porphyrins (Lim et al. (1988)), metalloporphyrins (Wan et al. (1994); Ho et al. (1994); Sato et al. (1994); and Beukeveld et al. (1994)), porphyrin dimers and trimers (Owens et al. (1996)), porphyrin isomers (Richter et al. (1992) and Udagawa et al. (1982)), and some porphyrin enantiomers (Kimmett et al. (1992) and Walker et al. (1988)). The large number of biological samples that need to be assayed during a typical pharmacokinetic study and the labor-intensive procedures in these HPLC techniques, required alternative methodologies for this kind of separation. Capillary electrophoresis (CE) is not new (Hjerten et al. (1967) and Jorgenson et al. (1981)) and there have been numerous subsequent studies (Wallingford and Ewing (1988); Pietta et al. (1994); Morin et al. (1993); Honda et al. (1990); Honda et al. (1989); and Hoffstetter-Kuhn et al. (1991)). The good reproducibility, sensitivity, rapidity, ease of automation and small sample requirements of CE have made it a promising bioanalytical technique (Kuhn et al. (1993)) for the separation of porphyrins and their analogues (Kuhn et al. (1993); Yao et al. (1996); Weinberger et al. (1990); Liu et al. (1995); Bowser (1996); and Bowser et al. (1997)). It has been especially useful in the separation of porphyrins because porphyrin fluorescence permits detection at low concentration.

Given the importance of BPDs in PDT and the desire to prepare specific stereoisomers for pharmaceutical, research and commercial/industrial applications, the present invention relates to a new CE method for the separation of BPD stereoisomers.

SUMMARY OF THE INVENTION

The invention is directed to the use of capillary electrophoresis (CE) methods for the rapid and reliable separation of benzoporphyrin derivative (BPD) stereoisomers, which can then be used in photodynamic therapy (PDT). In particular, laser-induced fluorescence mediated detection is used in combination with CE methods to improve the sensitivity and selectivity in the separation of stereoisomers of BPDs. Additionally, the methods of the invention can be used to completely separate with baseline separation enantiomers of BPDs (as presented in U.S. Pat. No. 5,171,749, which is hereby incorporated by reference as if fully set forth) as well as the derivatives of these compounds, especially the four enantiomers of BPD-monoacid (BPD-MA) and the two of BPD-diacid (BPD-DA), with high resolution and efficiency. Additional BPDs for separation are EA6 (as set forth in related application Ser. No. 08/852,494, which is hereby incorporated by reference as if fully set forth) and B3 (as set forth in related application Ser. No. 09/265,245, which is hereby incorporated by reference as if fully set forth).

The invention is also directed to methods of separating BPD stereoisomers as a preparative or analytical application. Because of superiority over known HPLC methods, the preparative or analytical applications of the invention include automated versions of the instant CE methods as well as versions utilizing a smaller sample size over traditional HPLC separation methods. Of particular preference is the use of the instant methods for the analysis of clinical samples of material containing BPDs.

Additionally, the invention includes the use of borate as a buffering system and cholate as a chiral selector for the separation of porphyrin compounds, including metalloporphyrins, porphyrin multimers and isomers, as well as the stereoisomers of such compounds. Borate and cholate can dynamically interact and complex with the BPD enantiomers and influence their electrophoretic properties and migration behavior. Particularly preferred conditions in such separations include the use of a capillary of 50 μm inner diameter and a 37 cm length (30 cm to detector), a field strength of +20 KV, a separation temperature of 20° C., a pH of 9.2, a borate concentration of 300 mM, 25 mM sodium cholate as a chiral selector, and 10% acetonitrile. A preferred baseline separation time is within 20 minutes.

Moreover, and beyond complete separation of enantiomers, the invention encompasses methods of separating the stereoisomers of different compounds, the regioisomers of a given compound, as well as the enantiomers of a given compound.

BRIEF DESCRIPTION OF THE DRAWINGS

The present invention will be more clearly understood by referring to the following drawings.

Benzoporphyrin derivative monoacids (BPD-MA, Ia-1, Ia-2, Ib-1, Ib-2) and benzo-porphyrin derivative diacid (BPD-DA, II-1, II-2). I and II designate BPD monoacid and diacid, respectively; a and b represent diastereoisomers; and 1 and 2 represent enantiomers.

Figure 2A:
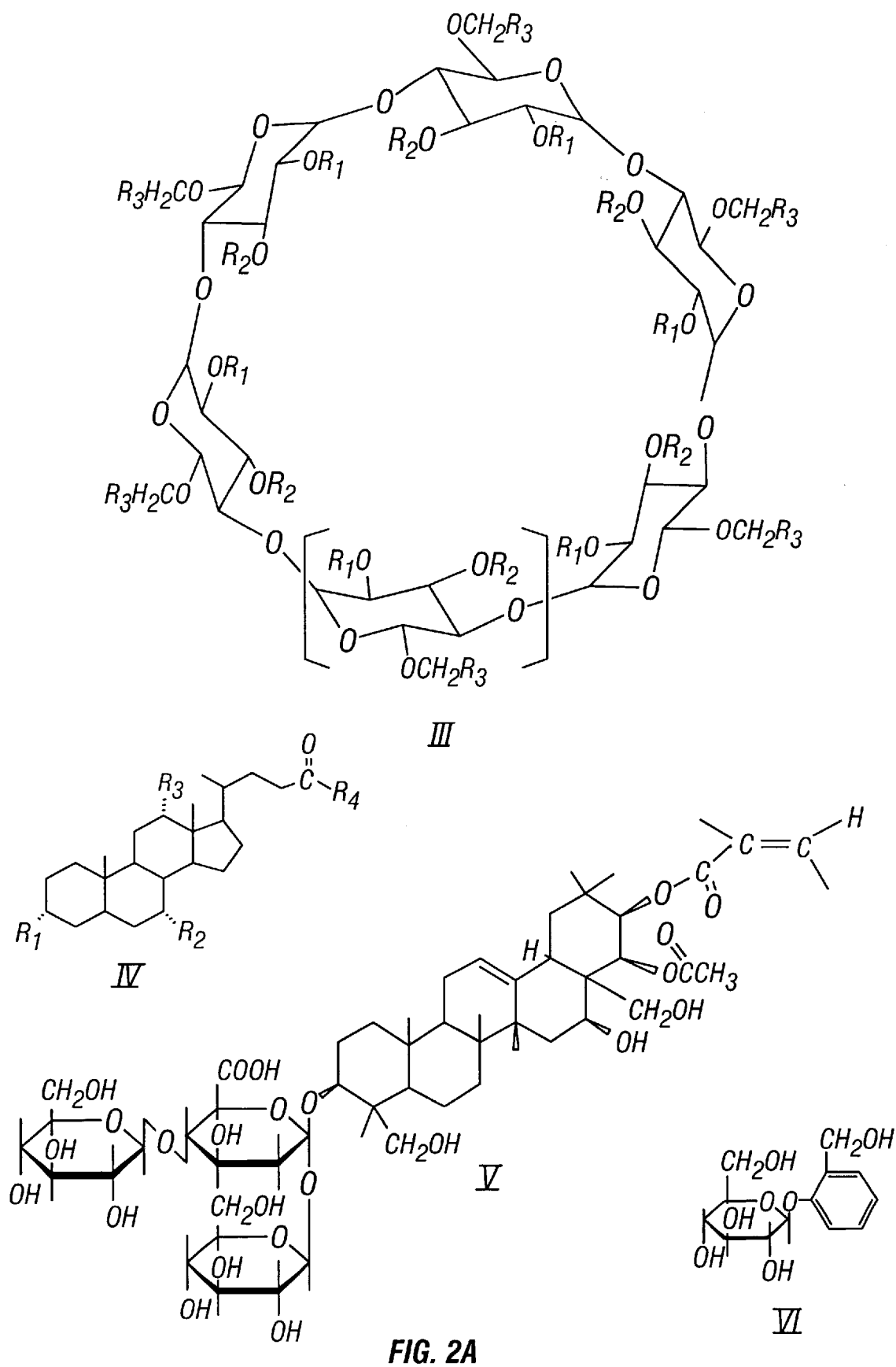
Figure 2B:
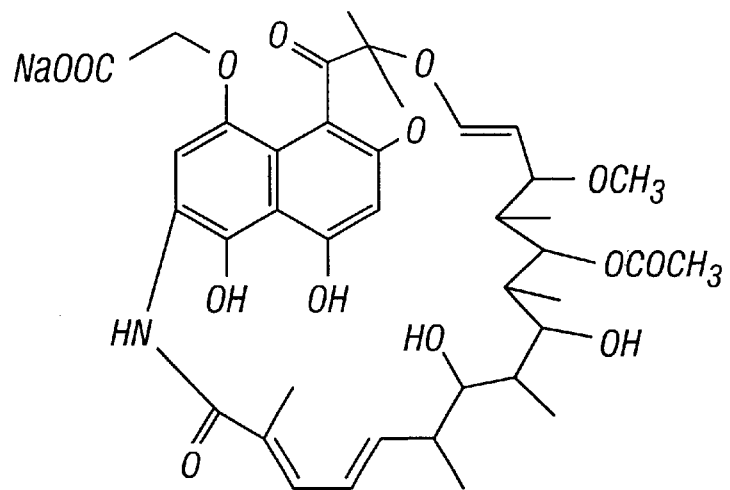
Figure 2B:
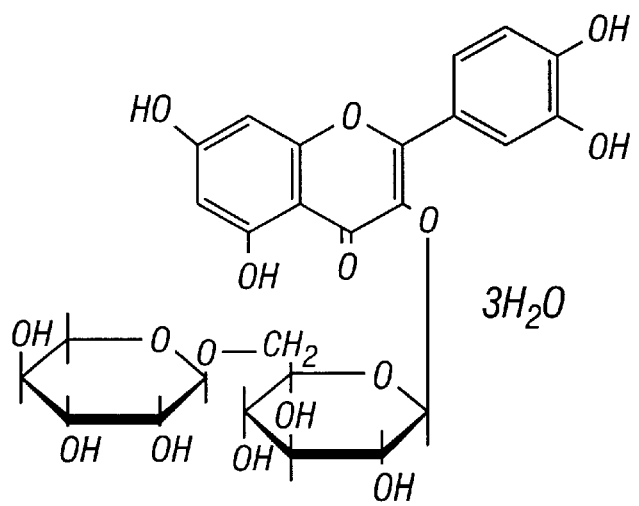
Figure 2B:
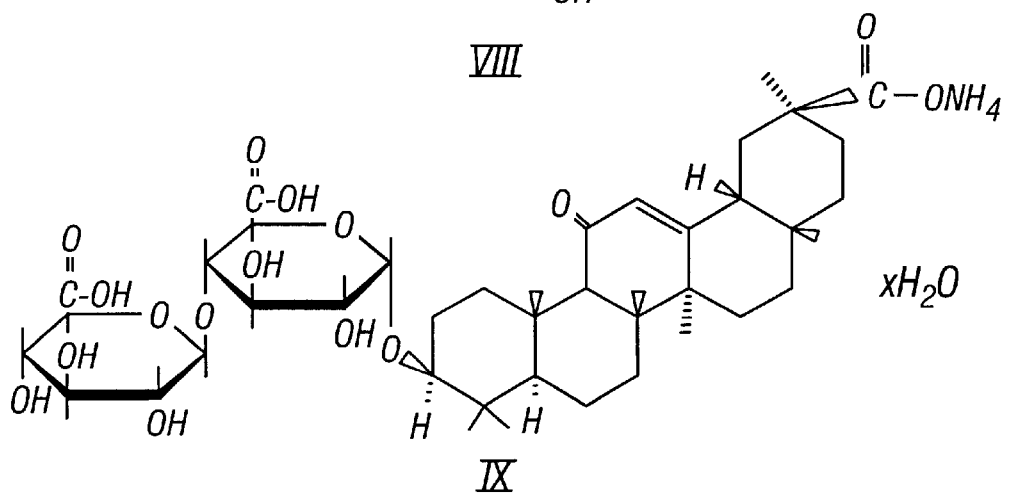

FIGS. 2A and 2B Structures of chiral additives

Hydroxypropal-β-cyclodextrin (III, n=2, $R_1=R_2=H$, $R_3$=hydroxypropyl); heptakis (2,6-di-O-methyl)-β-cyclodextrin (III, n=2, $R_1=R_3$=methyl $R_3$=H); β-cyclodextrin (III, n=2, $R_1=R_2=R_3=H$); γ-cyclodextrin (III, n=3, $R_1=R_2=R_3=H$); cholic acid, sodium salt (IV, $R_1=R_2=R_3=OH$, $R_4=ONa$); deoxycholic acid, sodium salt (IV, $R_1=R_3=OH$, $R_2=H$, $R_4=ONa$); tauocholic acid, sodium salt (IV, $R_1=R_2=R_3=OH$, $R_4=NH(CH_2)SO_3Na$); taurodeoxycholic acid, sodium salt (IV, $R_1=R_3=OH$, $R_2=H$, $R_4=NH(CH_2)_2SO_3Na$); β-exin (V); salicin (VI); rifamycin SV, sodium salt (VII); (+)-rutin hydrate (VIII); glycyrrizic acid (IX).

Figure 3:
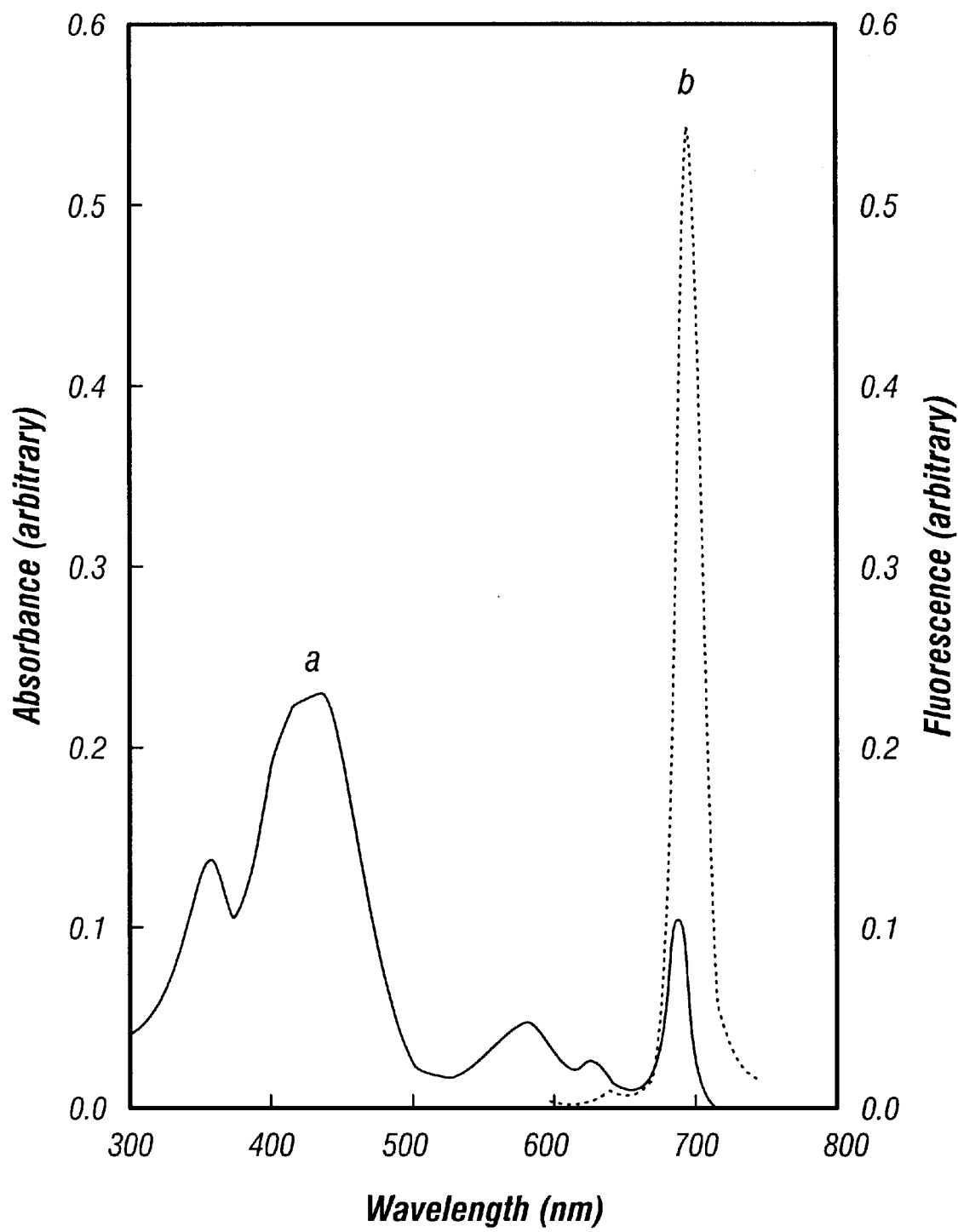

FIG. 3 UV-Vis and Fluorescence spectra of BPD-MA and BPD-DA a. UV-vis spectra, $1.0 \times 10^{-3}$ mg ml$^{-1}$ BPD-MA. b. Fluorescence emission spectra, BPD-MA $1.25 \times 10^{-4}$ mg ml$^{-1}$ at pH 9.2, 300 mM borate, 25 mM Cholate and 10% acetonitrile solution. BPD-DA exhibits similar spectra.

Figure 4:
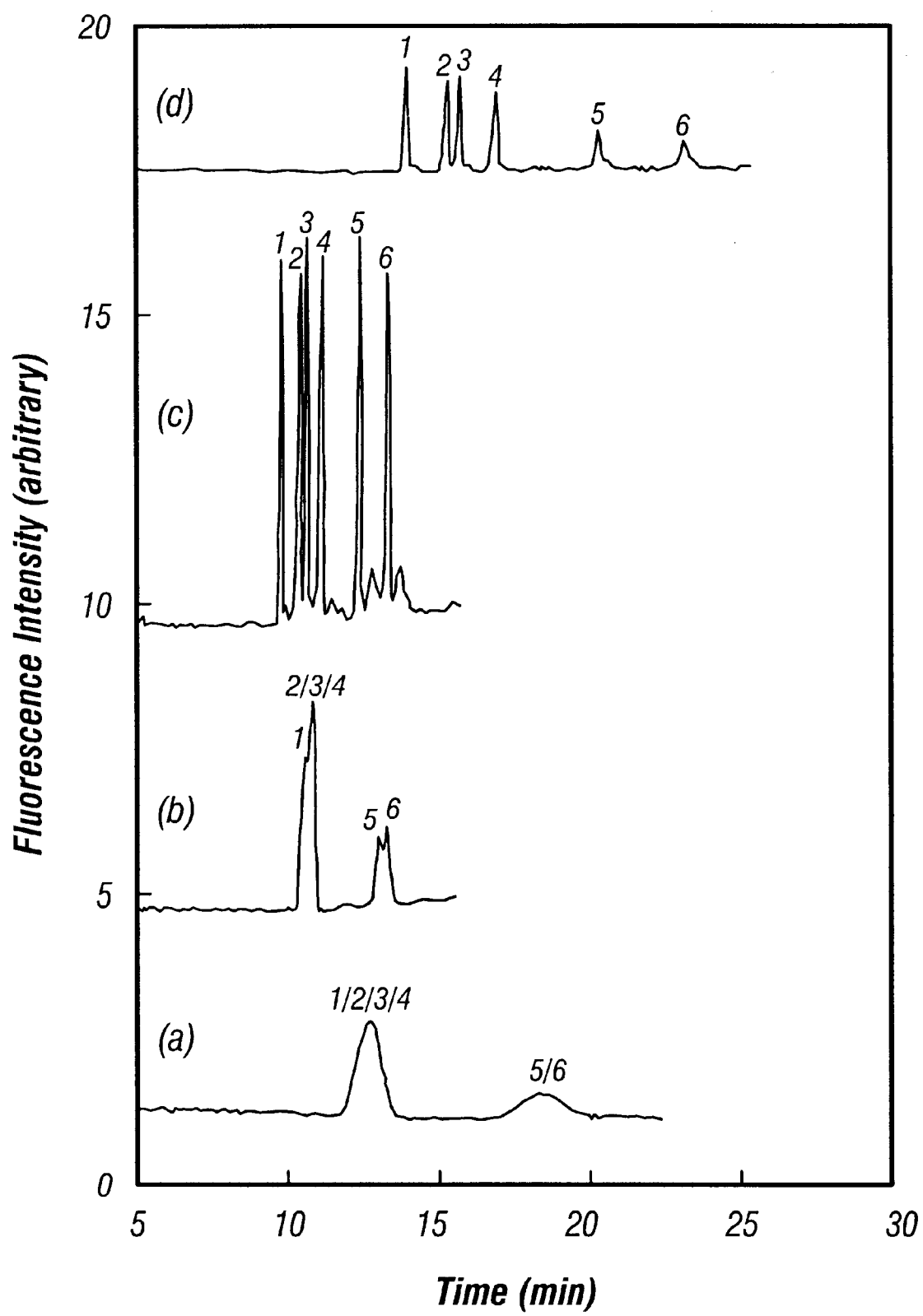

FIG. 4 Effect of buffer pH on BPD-MA and BPD-DA separation a. pH 8.05, b. pH 8.60, c. pH 9.2, d. pH 9.60. 300 mM borate and 25 mM sodium cholate and 10% acetonitrile. BPD-DA $2.5 \times 10^{-2}$ mg ml$^{-1}$, respectively. Em. 694nm/Ex. 488 nm. Data 5 Hz.+20KV, 37 cm, 20° C., electrokinetic sampling 2.0 s. Identificatin of peaks: 1, Ia-1; 2, Ib-1; 3, Ia-2; 4, Ib-2; 5, II-1; 6, II-2.

Figure 5:
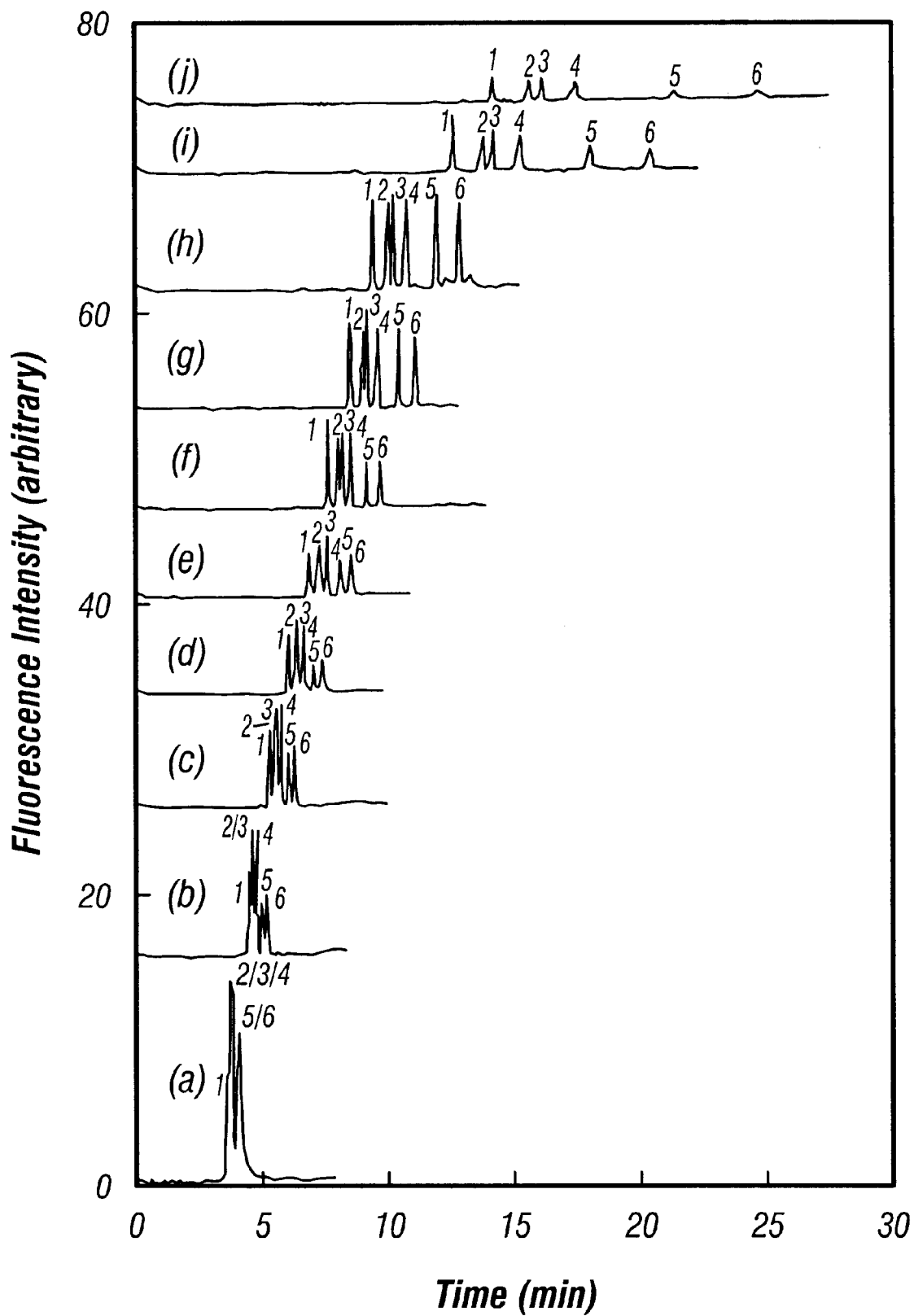

FIG. 5 Effect of electrolyte concentration on BPD-MA and BPD-DA separation a. 40 mM, b. 80 mM, c. 120 mM. d. 160 mM, e. 200 mM, f. 240 mM, g. 280 mM, h. 300 mM, i. 320 mM, j. 360 mM. borate (pH 9.2). Each contained 25 mM sodium cholate and 10% acetonitrile. BPD-DA $2.5 \times 10^{-2}$ mg ml$^{-1}$, respectively. Em. 694 nm/Ex. 488 nm. Data 5 Hz. +20 KV, 37 cm, 20° C., electrokinetic sampling 2.0 s. Identification of peaks is the same as in FIG. 4.

Figure 6:
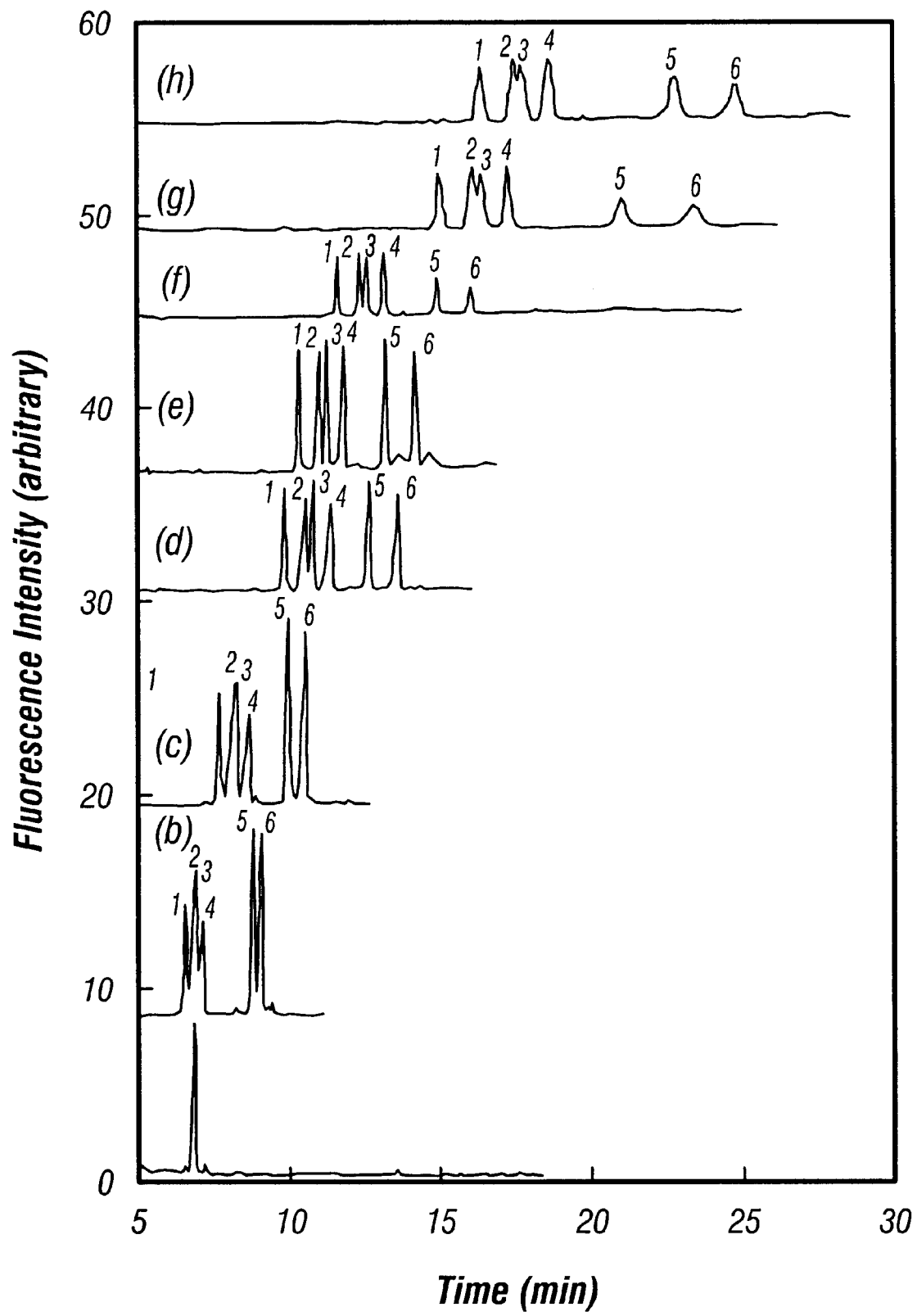

FIG. 6 Effect of sodium cholate on BPD-MA and BPD-DA separation a. 0 mM, b. 10 mM, c. 15 mM, d. 20 mM, e. 25 mM, f. 30 mM, g. 35 mM, h. 40 mM sodium cholate, pH 9.2, 300 mM borate and 10% acetonitrile. BPD-DA 2.5× $10^{-2}$ mg Ml$^{-1}$, respectively. Em. 694nm/Ex. 488 nm. Data 5 Hz. +20KV, 37 cm, 20° C., electrokinetic sampling 2.0 s. Identification of peaks is the same as in FIG. 4.

Figure 7:
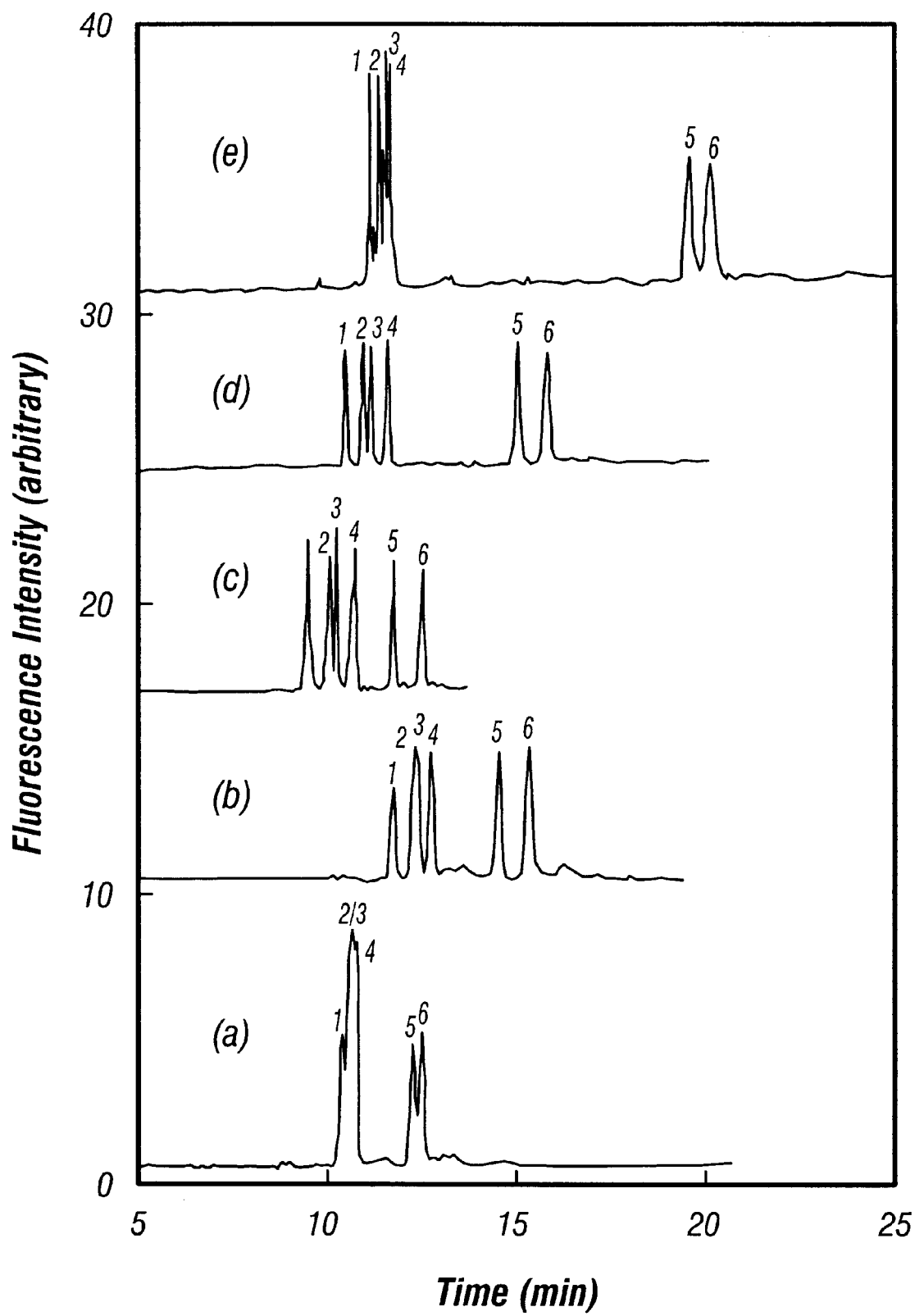

FIG. 7 Effect of acetonitrile a. 0%, b. 5%, c. 10%, d. 15%, e. 20% acetonitrile, pH 9.2, 300 mM borate and 25 mM sodium cholate. BPD-DA $2.5 \times 10^{-2}$ mg ml$^{-1}$, respectively. Em. 694 nm/Ex. 488 nm. Data 5 Hz. +20 KV, 37 cm, 20° C., electrokinetic sampling 2.0 s. Identification of peaks is the same as in FIG. 4.

Figure 8A:
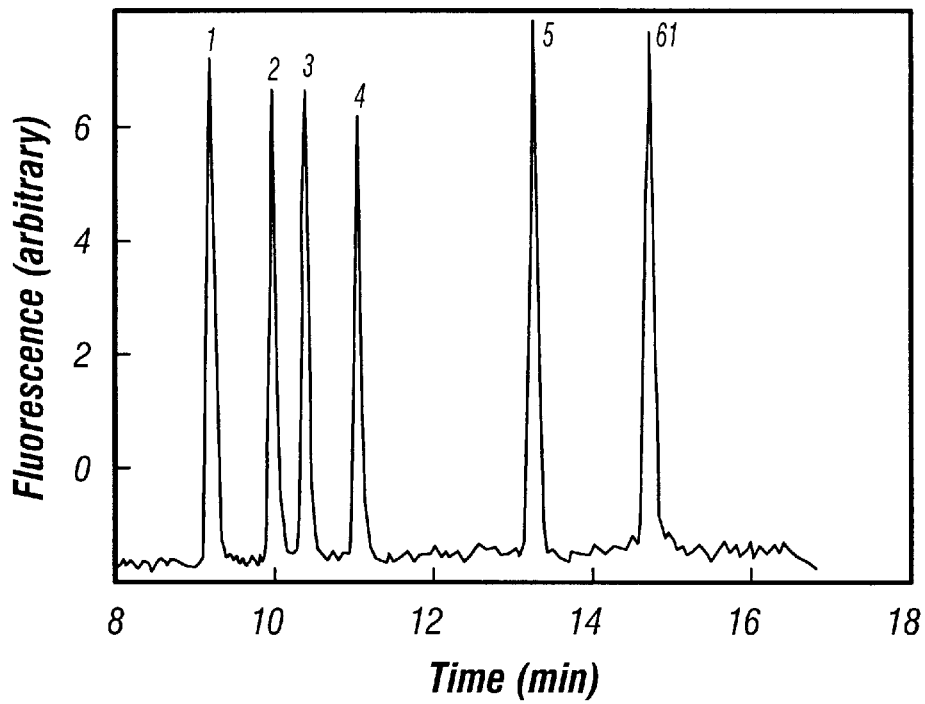
Figure 8B:
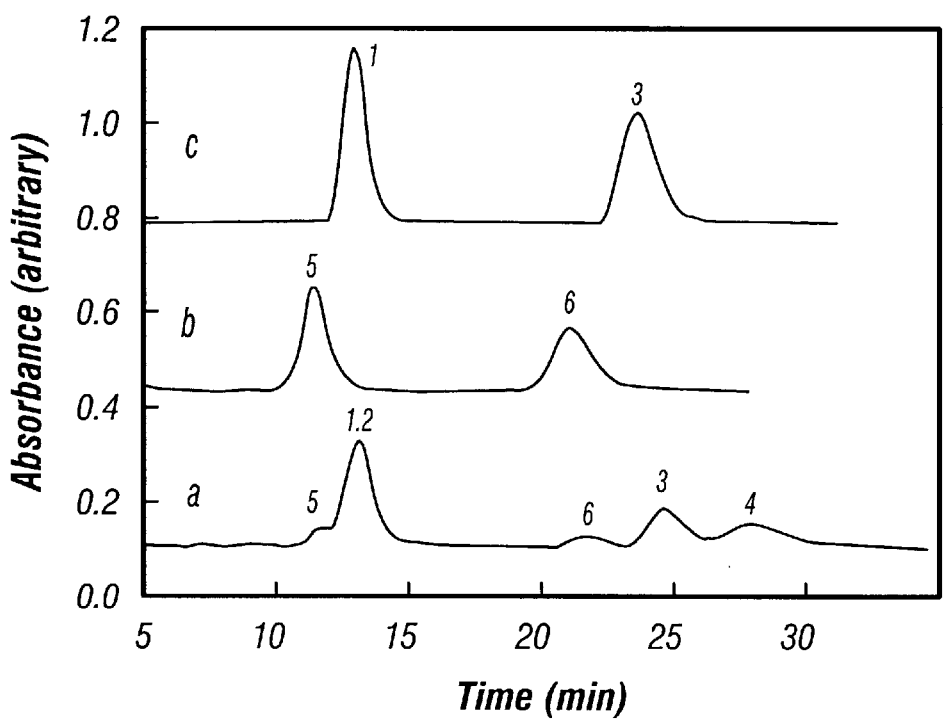

FIG. 8 Separation of BPD enantiomers by HPLC and CE

HPLC: a. BPD-MA/BPD-DA b. BPD-DA, c-BPD-MA. Elute is hexane: ethanol (80:20) containing 0.3% TTA. 0.7 ml min$^{-1}$ flow. Injection volume 50 μl of 0.1 mg ml$^{-1}$ of BPD-MA and BPD-DA. Detection at 420 nm. 1, Ia-2, 2, Ib-2, 3, Ia-1, 4, Ib-1, 5, II-2, 6, II-1.

CE: d. pH 9.2, 300 mM borate and 25 mM sodium cholate. BPD-MA/BPD-DA $2.5 \times 10^{-2}$ mg ml$^{-1}$, respectively. Em. 694 nm/Ex. 488 nm. Data 5 Hz. +20 KV, 37 cm, 20° C., electrokinetic sampling 2.0 s. Identification of peaks is the same as in FIG. 4.

Figure 9:
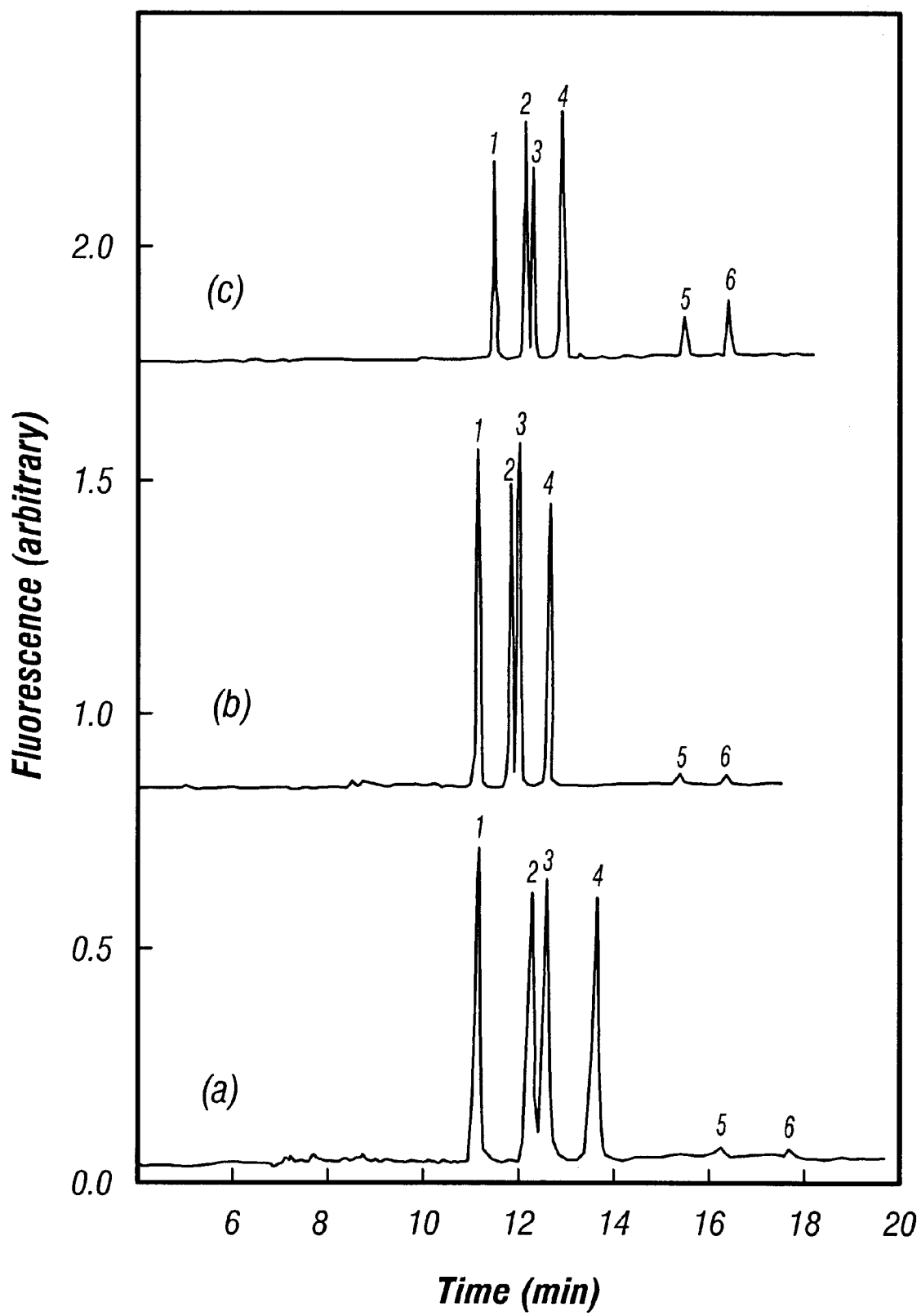

FIG. 9 Electrophoregram of BPD enantiomers

Liposomally formulated BPD-MA incubated with (a) dog, (b) human, and (c) rat liver microsomes for 120 min were used as samples. Identification of peaks is the same as in FIG. 4. pH 9.2, 300 mM borate and 25 mM sodium cholate. Em. 694nm/Ex. 488 nm. Data 5 Hz. +20KV, 37 cm, 20° C., electrokinetic sampling 2.0 s.

DETAILED DESCRIPTION OF THE INVENTION

The present invention embraces methods of using capillary electrophoresis (CE) to separate BPD stereoisomers, including separating with baseline separation, defined as no detectable overlap between the compounds being separated during elution. Preferred methods include using laser-induced fluorescence to improve detection and hence separation of the stereoisomers. These methods are of great utility in isolating BPD enantiomers while also offering greater flexibility for automation and use of smaller sample size over other separation methods. The most preferred use of the instant methods is for the isolation of the enantiomers of BPD-MA and BPD-DA, although the separation of other porphyrins are additional applications.

Preferred embodiments of the invention includes the use of borate as a buffering system and cholate as a chiral selector. Moreover, the invention is not limited to the complete separation of enantiomers. Instead, the methods of the invention may be used under conditions where the separation is sufficient to separate different compounds, to separate the regioisomers of a given compound, or to separate the enantiomers of a given compound.

Figure 1:
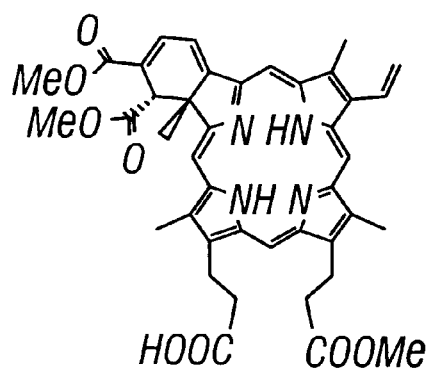
FIG. 1 Structures of the stereoisomers of BPD-MA and BPD-DA
Figure 1:
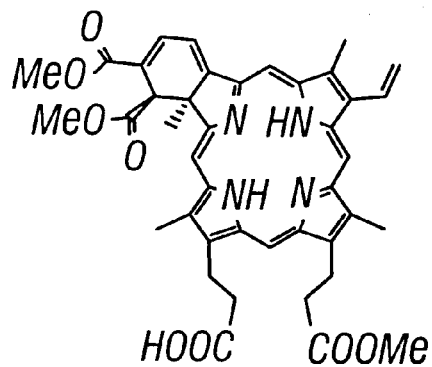
Figure 1:
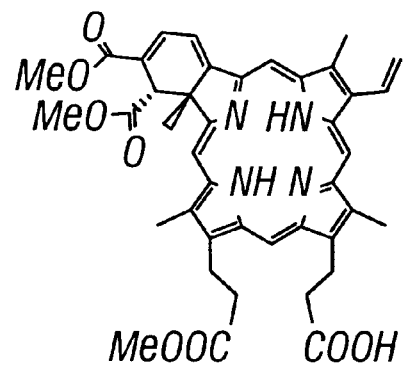
Figure 1:
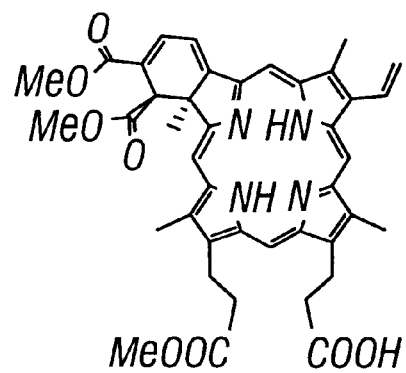
Figure 1:
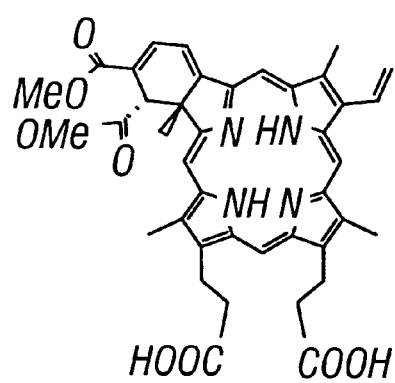
Figure 1:
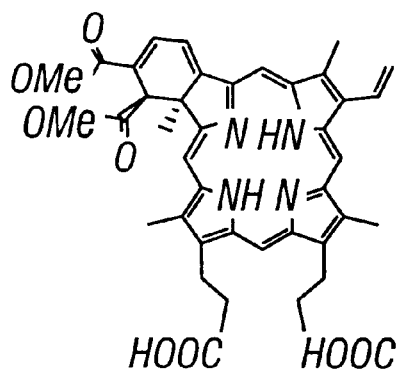

The separation methods of the invention are particularly useful for chlorin-like photosensitizer, such as BPD-MA. As used in the clinic, BPD-MA consists of an equal mixture of the two regioisomers (Ia, Ib). Each regioisomer consists of a pair of enantiomers (Ia-1, Ia-2; Ib-1, Ib-2) as shown in FIG. 1. The principal metabolite is the diacid which consists of two enantiomers (II-1, II-2). Tissue distribution studies and efficacy of the regioisomers have been reported (Richter (1991); Woodburn (1992); and Richter et al. (1988)). BPD-DA is composed of two enantiomers (FIG. 1).

The compounds have the same chromophore and identical absorption spectra (FIG. 3a) with a characteristic major broad peak in the Soret region (420 nm) and several other peaks at longer wavelengths. The most interesting long wavelength peak, in terms of applications in PDT, is the peak at 688 nm (in organic solvents). Extinction coefficients were determined at 430 nm in a buffer solution of 300 mM borate containing 10% acetonitrile and 25 mM sodium cholate pH 9.2 and found to be 61,000 $M^{-1}cm^{-1}$ and 75,200 $M^{-1}cm^{-1}$ for BPD-MA and BPD-DA, respectively. An emission spectrum is also shown in FIG. 3b with a characteristic emission at about 692 nm, near red (Q-band), with a Stokes shift of ~4 nm for fluorescence. Given the above, there are no apparent mechanistic difference in photo absorption, and hence BPD mediated damage, between the various stereoisomers of each BPD compound. As such, there is no gain in photo absorption by use of any particular BPD enantiomer.

At low pH the free base porphyrin pyrroles can be protonated to yield the $PH_3^+$ or $PH_4^{2+}$ forms. At pH greater than about 3.0, the free bases are neutral, and only the side chain propionic acid residues are protonated. At higher pH, propionic acid side chains can be ionized to give a $P^-$ for BPD-MA or $P^{2-}$ for BPD-DA. The charges on these compounds play an important role in their separation by capillary electrophoresis.

Capillary electrophoresis

Separation by capillary electrophoresis is based on differential mobilities. Experimental parameters which affect mobility include capillary inner diameter and length, separation voltage, temperature, buffer type and concentration, pH, ionic strength, chiral selector type and concentration, organic solvent type and amount in the electrolyte. Additionally, the size, net charge and the interaction of the analytes with additives affect mobility in capillary electrophoresis. Size and charge of the analytes are related to their molecular mass, structure and the degree of hydration and ionization. The involvement of and interaction between these various parameters are known to the skilled artisan and can be routinely evaluated and optimized. Thus, the selection of appropriate diameters, lengths, voltages, temperatures, buffer types and concentration, pH, ionic strength, chiral selector type and concentration, organic solvent and amount, and other parameters can be selected without undue experimentation Initial CE parameters to consider include capillary inner diameter and length as well as separation voltage. In evaluating CE for the BPD enantiomers, a +10 KV electrokinetic injection of about 2.0 s was applied, although a range of about +10 to about +25 KV may be used in longer or shorter time intervals. The BPD enantiomers enter the capillary by both migration and by the pumping action of the electroosmotic flow (EOF). Additionally, electrokinetic injection helps concentrate the samples by a "stacking" phenomenon. This injection method is especially beneficial for biological matrices or clinical samples which usually contain large amounts of sodium chloride.

Small inner diameter capillaries can more readily dissipate the joule heating and lower the electric current to result in better separation efficiency. A capillary of about 50 $\mu$m inner diameter is preferred for BPD enantiomers, although inner diameters ranging from about 40 to about 75 $\mu$m may also be used. Small inner diameters often leads to strong inner capillary wall adsorption along with increased clogging. The detection sensitivity also decreases with a shorter detection window. Proper conditioning of the capillary and filtration of the running buffer are necessary normal steps before each run.

In order to apply very high electric fields and to decrease the analyte migration time, an appropriate capillary length is necessary. The separation time of the six BPD enantiomers was about 45 min using a capillary of about 57 cm but with a capillary length of about 27 cm, the migration time decreased to about 5 min. As such, a range of lengths from about 27 to about 57 cm may be used. The separation efficiency also decreased since the BPD enantiomers migrated very rapidly past the detection window and did not have sufficient time to separate. A good separation of BPD compounds with an acceptable time profile was obtained using a preferred capillary of about 37 cm in length.

The electroosmotic flow and electrophoretic migration velocity are directly proportional to the field strength applied across the capillary. High field strengths lead to shorter migration times, and a range of about +10 to +25 KV may be used. Three field strengths were compared for the separation of the BPD enantiomers. At about +15 KV, BPD peaks 2 and 3 (the peaks are defined in FIG. 4) were overlapping after about 25 min. This may have been due to diffusion. By increasing the voltage to about +20 KV, all six BPD enantiomers were baseline separated within about 15 min. When the separation voltage was increased to about +25 KV, the migration time became shorter but high current and joule heating caused sample plug diffusion and peaks 2 and 3 once again overlapped. In addition, joule heating caused a temperature increase in the inner capillary which resulted in a signal decrease as the BPD fluorescence quantum yields decreased. A field strength of about +20 KV is preferred to give complete baseline separation for all six enantiomers.

Another parameter in CE is temperature. Elevated or reduced separation temperatures can alter running buffer viscosity, electroosmotic flow and analysis time; analyte chemical equilibrium and kinetics in the separation process can also be affected. A range from about 10 to about 35° C. may be used. When the temperature was increased from about 25° C. to about 35° C., migration time became shorter due to a decrease in the running buffer viscosity which consequently caused the EOF to decrease. At about 35° C., peaks 2 and 3 once again overlapped as a consequence of joule heating which caused non-uniform temperature gradients, local changes in viscosity and density, and gave rise to zone deformation and subsequent zone broadening. The P/ACE 5500 has a thermostat system range from 5 to 50° C., although at about 15° C., the separation showed significant improvement, and it took about 15 minutes to reach equilibrium. A temperature of about 20° C. is preferred as the separation temperature.

Separation by CE is also affected by the buffering system used. Buffer type, concentration, ionic strength, and pH are all parameters to consider, and a variety of buffers may be used. Buffer solutions of pH 11.04, 100 mM 3-(cyclohexylamino)-1-propanesulfonic acid (CAPS); pH 6.76, 30 mM ammonium acetate; pH 2.76, 50 mM citric acid; and pH 9.2, 100 mM borate were tested as electrolytes. The BPD enantiomers were very easily hydrolyzed at high pH using the CAPS buffer (~pH>11); high concentrations of ammonium acetate buffer usually caused bubbles in the capillary which led to current breaks. This was followed by either separation shut down or excess spiking and signal noise. In citric acid buffer the BPD enantiomers were protonated at the propionic side chain, defeating separation based on the deprotonated state. Since the effective charge(s) are the same for BPD-DA and BPD-MA, the electrophoretic mobility difference is normally very small. Also, at high pH, the EOF was very small and this caused the migration time to become overly long. The result was very poor signal separation due to extensive diffusion.

With borate buffer at about pH 9.2, however, the BPD-DA and BPD-MA enantiomers were completely separated. This, in combination with the ability of borate to form a very stable buffer solution with high buffering capacity and its ability to be used in very high concentrations, made it a preferred choice for use in the instant separation methods. Borate has also been used in other separation systems (Consden et al. (1952); Boeseken (1949); and Landers et al. (1992)). Moreover, studies have shown that BPD-MA decomposed less than 1% in one hour at pH 9.2. Therefore, decomposition (principally hydrolysis) can be ignored within the approximately 15 min analysis time of capillary electrophoresis in borate.

The side chain propionic acid of BPD enantiomers begin to deprotonate when the pH of borate buffer was above about 3.5. As such, pH's above about 3.5 are preferred in the CE methods of the invention. Preferred pH's range from about 8.05 to about 9.6. BPD-MA enantiomers have one ionizable carboxylic acid group, and BPD-DA has two acidic groups. This charge difference makes BPD-MA and BPD-DA readily separated by CE. In addition to the BPD-MA and BPD-DA separation, differences in pH also alter the dynamic complexation of the BPD enantiomers with chiral selector additives, changing their mobility differences. FIG. 4 shows that only BPD-MA and BPD-DA were separated at pH 8.05. The BPD-DA and BPD-MA enantiomers were separated to some extent at pH 8.6, and complete separation was achieved at pH 9.2. By increasing the pH to 9.6, the BPD enantiomers were further distinguished, but their signals decreased due to the higher ionic strength, which adversely influenced fluorescence. Furthermore, migration times also increased due to the high ionic strength which inhibits the EOF.

The effects of borate ionic strength are shown in FIG. 5. One disadvantage of increasing ionic strength results from the current increase and excessive joule heating in the capillary. Positive attributes of increasing ionic strength include decreased adsorption of BPD enantiomers on the capillary wall and a suppression of electrophoretic dispersion. It also reduces the EOF and makes the analytes migrate slower to provide better separation. Higher ionic strength also increased the dynamic complexation of borate with the BPD enantiomers and influenced the separation resolution. Ionic strengths ranging from 40 to 360 mM borate may be used in the instant methods, although a range of 120 to 360 mM is preferred, and a range of 200 to 360 mM is more preferred. Most preferred is an ionic strength of 300 mM. At high borate concentrations (above about 360 mM), the buffer solubility and stability deteriorated which caused current breaks and capillary clogging.

Formation constants, free electrophoretic and complexation mobilities with borate and cholate were determined based on dynamic complexation capillary electrophoresis theory (Peng et al. (1997)). The formation constants for dynamic complexation of BPD enantiomers with borate are given in Table 1. Formation constants (K) are in the range of about 11.51 to about 12.51, with little difference between enantiomers showing weak interactions in each case. Based on the equation proposed by Goodall's group (Penn et al. (1994)), the enantiomeric mobility difference ($\Delta\mu$) is proportional to the difference in the two enantiomeric formation constants ($\Delta K$) and the chiral additive concentration. Although $\Delta K$ for BPD-MA Ia-2 (K about 11.90) and BPD-MA Ib-1 (K about 11.91) is only 0.01, increasing the borate concentration from about 40 mM to about 360 mM, makes $\Delta\mu$ increase about 9 times and resolution of the two regioismers increases dramatically. It may also be possible that when borate interacts with BPD enantiomers, the complexes move slower than uncomplexed enantiomers. For example, the free state mobility BPD-MA Ia-1 is about $-1.95\times10^{-5}$ $cm^2V^{-1}s^{-1}$ while its complex mobility is about $-2.94\times10^{-5}$ $cm^2V^{-1}s^{-1}$. This means that when BPD-MA Ia-1 interacts with borate, the complex a has bigger ratio of charge to size (q/r, where q denotes charge and r denotes radius). Due to this size increase, BPD-MA Ia-1 becomes more negatively charged when complexed with borate. This leads to longer separation times. All of the other BPD enantiomers behave in a similar manner as BPD-MA Ia-1.

TABLE 1

Formation constant determinations for the BPD enantiomers with borate and cholate

| | Borate | | | | cholate | | | |
|---|---|---|---|---|---|---|---|---|
| | $\mu_{ep},A^a$ | $\mu_{ep},Ac^b$ | $K^c$ | $R^{2d}$ | $\mu_{ep},A^a$ | $\mu_{ep},Ac^b$ | $K^c$ | $R^{2d}$ |
| BPDMA (Ia-1) | −19.53 ± 0.64 | −29.39 ± 1.01 | 11.51 ± 1.68 | 0.9970 | −17.41 ± 0.57 | −33.55 ± 1.28 | 28.50 ± 3.50 | 0.9848 |
| BPDMA (Ia-2) | −21.15 ± 0.61 | −31.21 ± 1.00 | 11.90 ± 1.71 | 0.9970 | −17.41 ± 0.50 | −33.55 ± 1.38 | 30.54 ± 4.07 | 0.9801 |
| BPDMA (Ib-1) | −20.36 ± 0.52 | −30.33 ± 1.03 | 11.91 ± 1.78 | 0.9968 | −17.41 ± 0.45 | −33.29 ± 1.28 | 30.90 ± 3.90 | 0.9815 |
| BPDMA (Ib-2) | −22.27 ± 0.49 | −32.38 ± 0.99 | 12.27 ± 1.76 | 0.9969 | −17.41 ± 0.38 | −33.45 ± 1.41 | 36.53 ± 4.45 | 0.9768 |
| BPDDA (II-1) | −22.83 ± 0.54 | −33.19 ± 1.08 | 12.48 ± 1.90 | 0.9965 | −17.41 ± 0.41 | −30.75 ± 0.53 | 49.04 ± 3.73 | 0.9853 |
| BPDDA (II-2) | −25.80 ± 0.53 | −36.41 ± 1.07 | 12.51 ± 1.85 | 0.9966 | −17.41 ± 0.36 | −31.15 ± 0.62 | 48.42 ± 4.14 | 0.9828 |

[a]The electrophoretic mobility of analyte in free form ($\times 10^{-6}$ $cm^2V^{-1}s^{-1}$).
[b]The electrophoretic mobility of complex when analyte forms a complex with additive ($\times 10^{-6}$ $cm^2V^{-1}s^{-1}$).
[c]The formation constant was calculated according to the methods described in Peng et al. (1997).
[d]The correlation coefficients ($r^2$) of the least-squares linear regression analysis of BPD enantiomers formation constant.

Separation of the enantiomers by CE also involves a choice of chiral selectors (additives). These form diastereoisomeric pairs in a dynamic equilibrium complexation process which, if sufficiently distinct electrophoretically, allow for chiral separation. A wide range of chiral selectors for use in CE, such as metal complexes, micellar systems, micromulsions, crown ethers, cyclodextrins, oligosaccharides and proteins are known in the art (Aveline et al. (1995)) and may be used in the instant methods.

For BPD stereoisomers, different additives (shown in FIGS. 2A and 2B) HP-β-CD, DM-β-CD, β-CD, and γ-CD, bile salts, β-escin, salicin, sodium rifamycin SV, (+)-rutin hydrate and ammonium glycyrrhizic have been tested as chiral selectors. The bile salts are preferred chiral selector agents. Bile salts are biological surfactants and form small or primary aggregates of 3 to 14 monomers. These aggregates form a type of "inverse micelle" having a negatively charged core and a hydrophobic uncharged surface, which is opposite to that exhibited for sodium dodecyl sulfate (SDS). The amphiphilic nature of bile salts provides both hydrophobic and polar (or electrostatic) sites. The non-polar faces of the monomers aid in solubilizing hydrophobic compounds, and the structurally rigid chiral bile salts selectively interact with BPD enantiomers.

Four sodium bile salts: cholate, taurocholate, deoxycholate and taurodeoxycholate were further tested as chiral selectors. Small changes in their chemical structures (FIGS. 2A and 2B) had a significantly impact on the recognition of BPD enantiomers, but all four may be used in the methods of the invention. Sodium cholate had the best separating ability (FIG. 6) and is the most preferred chiral selector, although other salts of cholate may also be used. Moreover, a range of bile salt concentrations, ranging from about 10 to about 35 mM may be used. Increasing the sodium cholate concentration from 0 mM to about 10 mM allowed for the separation of BPD-MA and BPD-DA with only partial separation of their enantiomers. By increasing the sodium cholate concentrations to about 15 and then about 20 mM, the two BPD-DA enantiomers gave complete baseline separation within approximately 11 min, while the BPD-MA enantiomers showed four peaks, two of them overlapping. By further increasing the sodium cholate concentration to about 25 and about 30 mM, complete baseline separation of both the four BPD-MA and the two BPD-DA enantiomers was observed. A preferred sodium cholate concentration for the separation is about 25 mM, although a range from about 15 to about 30 mM. When the sodium cholate concentration was greater than about 30 mM, all peaks were shifted to longer analysis times with deterioration in resolution (FIG. 6).

The formation constants (K) of sodium cholate with the BPD enantiomers were determined to be about 28.5, 30.54, 30.90, 36.53, 49.04, 48.42 (Table 1). Differences in the formation constants makes the separation of all six enantiomers possible, and optimization of the cholate concentration allows for optimal separation. The complex mobilities of the enantiomers with cholate have more negative values than the corresponding enantiomers in their free uncomplexed state (Table 1).

Organic solvents can also alter the polarity and viscosity of a buffer electrolyte, resulting in changes to both the electrophoretic mobility and EOF. Organic solvents are also widely used as a solubilizing agent for analytes which are poorly soluble in aqueous solution, for increasing solvation of solutes, and for modifying the affinities of hydrophobic solutes. BPD derivatives undergo self-aggregation in aqueous media, but this can be prevented by adding organic solvent (Aveline (1995)). As such, any organic solvent may be used in the methods of the invention. The effects of acetonitrile, dimethyl formamide (DMF), methanol, dimethyl sulfoxide (DMSO), n-propanol and isopropanol were evaluated. It was found that the BPD enantiomers can be baseline separated upon the addition of DMF, isopropanol or acetonitrile. All tested organic solvents exhibited synergetic effects which improved the separation. FIG. 7 shows the results of changing acetonitrile concentration in the running buffer. Acetonitrile in amounts from about 10 to about 15% are preferred to enhance separation (FIG. 7). Without the addition of acetonitrile or another organic solvent, aggregation prevents separation. When acetonitrile was above about 20%, the running buffer electrolyte became unstable, with both borate and sodium cholate precipitation leading to capillary clogging.

Reproducibility in CE is highly desirable for efficient separation. Thus proper capillary conditioning methods and analytical procedures are important to maintain a reproducible capillary surface and to obtain reproducible separations. Conditioning refreshes the surface, deprotonates the silanol groups, and removes absorbed impurities. BPD enantiomers exhibit strong adsorption on silica. A sufficiently long rinse time prevents the capillary inner wall from building a contact coating. Too short a rinse time results in the contact coating reducing EOF. This results in longer sample migration times, and causes band broadening and tailing, thus impairing separation. The example section below sets forth a preferred conditioning method, which performed well as shown in Table 2, with relative standard deviation (RSD) only between 2.90% to 4.64%. The contribution of the charged BPD enantiomers to the overall ionic strength of the run electrolyte and the amount of DMSO in the sample can be ignored because of their very low concentrations.

TABLE 2

Results from linearity studies

| Analytes | Equation[a] | Range (mg ml$^{-1}$) | $R^2$ | RSD %[b] | DL[c] ($\times 10^{-6}$M) |
|---|---|---|---|---|---|
| BPDMA (Ia-1) | Y = 103.46X + 0.20 | $5 \times 10^{-2}$–$5 \times 10^{-5}$ | 0.9973 | 4.64 | 3.25 |
| BPDMA (Ia-2) | Y = 99.827X + 0.24 | $5 \times 10^{-2}$–$5 \times 10^{-5}$ | 0.9986 | 4.09 | 2.85 |
| BPDMA (Ib-1) | Y = 89.027X + 0.19 | $5 \times 10^{-2}$–$5 \times 10^{-5}$ | 0.9990 | 3.67 | 2.56 |
| BPDMA (Ib-2) | Y = 117.32X + 0.25 | $5 \times 10^{-2}$–$5 \times 10^{-5}$ | 0.9997 | 3.12 | 2.18 |
| BPDDA (II-1) | Y = 491.68X + 1.17 | $5 \times 10^{-2}$–$5 \times 10^{-5}$ | 0.9914 | 3.32 | 2.36 |
| BPDDA (II-2) | Y = 532.57X + 1.37 | $5 \times 10^{-2}$–$5 \times 10^{-5}$ | 0.9910 | 2.90 | 2.06 |

[a]Calibration curve equation for BPD-MA enantiomers.
[b]Means of ten determinations each, with 95% confidence limits.
[c]Detection of limits is the concentration of analytes that give a signal equal to twice the peak-to-peak noise level of the analytes.

High sensitivity laser-induced fluorescence greatly improves the sensitivity and selectivity of BPD stereoisomer separation by CE. Although the smaller inner diameter capillary of about 50 nm resulted in a decrease of analytical signal it also prevents temperature increases due to high currents. The excessive joule heating observed with a 75 nm inner diameter capillary lowers the quantum efficiency of fluorescence due to the increased frequency of collisions at elevated temperature and deactivation by external conversion. The addition of acetonitrile also prevents BPD aggregation and self-quenching and self-adsorption, which otherwise results in an unusual analytical signal.

A wavelength bandpass filter at 690 ±5 nm may also be used to remove the background noise and other interference. The multiple absorption bands of the BPD derivatives permits the use of a 488 nm laser for excitation. Most matrix (or otherwise contaminating) compounds in clinical samples do not absorb at about 488 nm, nor fluorescence at 690 nm. Matrix influence also can be prevented, to some extent, by using the electrokinetic injection mode.

A calibration curve facilitates CE separation. Calibration graphs for concentrations of $5.0 \times 10^{-5}$ M to $5.0 \times 10^{-2}$ M BPD were used for the analysis of BPD enantiomers in field samples. Samples were injected in triplicate, and average peak areas, instead of peak heights, were used to construct the calibration curves. The correlation coefficients ($r^2$) from a least-squares linear regression analysis of the BPD enantiomers ranged from 0.9814 to 0.9997 and are listed in Table 3. The limits of detection were from $2.06 \times 10^{-6}$ to $3.25 \times 10^{-6}$ M for the BPD enantiomers with a signal-to-noise ratio of 2:1 at a detection wavelength of 694 nm. The same day relative standard deviations were from 2.90% to 4.64% (n=10).

A comparison of HPLC and CE for the separation of BPD stereoisomers demonstrates a significant superiority in CE. With HPLC, the optimal conditions were found to be hexane:ethanol (80:20, 1% diethylamine), 0.7 mL min$^{-1}$ flow rate and 50 $\mu$l of a 0.1 mg mL$^{-1}$ BPD solution. Using a Chiral Pak AD column, BPD-MA(I), BPD-MA(II) and BPD-DA enantiomers were separated (FIG. 8). When BPD-MA and BPD-DA were mixed and injected. BPD-MA (I) and BPD-MA (II) completely overlapped and BPD-DA partly overlapped with BPD-MA (I, II). The peak shapes were distorted by tailing, and the analytical migration time was as long as 35 min. In comparison to the separation electrophoragram of the BPD enantiomers performed by CE (FIG. 8), the CE method made a significantly improvement in resolution. The analytical time was shortened to 13 min. with completely baseline separation of all the BPD enantiomers and sharp peaks were observed without tailing. The resolution and number of theoretical plates (N) per meter of capillary are listed in Table 3. N/m is in the range of 46100 to 115400 in CE. This may be considered as satisfactory, especially compared with chiral HPLC analysis where N/m is no more than 1650.

TABLE 3

Comparison of the Separation of BPD enantiomers by HPLC and CE

| | CE | | | HPLC | | |
|---|---|---|---|---|---|---|
| | $t^a$ (min) | $N^b$ (× 10$^4$) | Rs$^f$ | $t^a$ (min) | $N^b$ (× 10$^2$) | Rs$^f$ |
| BPDMA (Ia-1) | 9.38 | 9.96 | 8.20$^c$ | 12.31 | 11.40 | 3.72$^c$ |
| BPDMA (Ib-1) | 9.95 | 4.82 | 2.92$^d$ | 12.70 | 6.43 | 1.79$^d$ |
| BPDMA (Ia-2) | 10.17 | 10.41 | — | 24.05 | 16.52 | — |
| BPDMA (Ib-2) | 10.64 | 4.61 | — | 27.64 | 5.46 | — |
| BPDDA (I-1) | 11.79 | 11.54 | 4.17$^e$ | 11.70 | 7.49 | 3.05$^e$ |
| BPDDA (II-2) | 12.61 | 10.48 | — | 21.69 | 8.60 | — |

$^a$Migration time.
$^b$The number of theoretical plates. N = $5.54(t/w_{1/2})^2$
$^c$The resolution of peaks BPD-MA (Ia-1) and BPD-MA (Ia-2)
$^d$The resolution of peaks BPD-MA (Ib-1) and BPD-MA (Ib-2)
$^e$The resolution of peaks BPD-DA (II-1) and BPD-DA (II-2)
$^f$The resolution of two peaks, Rs = $2(t_2 - t_1)/(w_2 + w_1)$ Applications The methods of the instant invention may be used to separate BPD stereoisomers. Such separation techniques may be used to prepare specific stereoisomers, regioisomers or enantiomers for use in research, testing, or therapeutic applications. Alternatively, the methods may be used in analytical applications to identify particular stereoisomers from mixtures or complex samples. These analytical applications include the use of the instant invention to quantify the amounts of particular stereoisomers in a given sample. These applications can be used in studies of BPD delivery and metabolism in clinical samples of various tissues over time. As such, they are of great potential value in medical and therapeutic applications.

One analytical application is extraction of BPD from bovine serum. The recovery using acetonitrile (×3) in CE is about 91.2%. Initial purification of the extracts, such as with a Waters Sep-Pak cartridge, removes most of the matrix components (such as proteins, salts, etc.). After concentration, the samples can be directly injected for CE analysis. The evaporation step is necessary for sample preparation, since this allows for precipitation and removal of additional impurities. The main disadvantage of the sample preparation using a Sep-pack cartridge is the partial hydrolysis to BPD-DA enantiomers if the pH is not well controlled (pH must be maintained between 6.0 and 8.0). An alternative method was developed by replacing the Sep-Pak cartridge with a 0.22 $\mu$m solvent filter. A standard solution of liposomally formulated drug (Verteporfin, BPD-MA) can be readily separated. Based on these techniques, the metabolites of liposomal formulated BPD-MA incubated with liver microsomes of rat, dog and human were successfully separated (FIG. 9).

The following examples are intended to illustrate but not to limit the invention.

EXAMPLE 1

Materials Used

Capillary Electrophoresis System and Instrumentation

All experiments were performed using a Beckman P/ACE 5500 system consisting of an autosampler, a vacuum injection system, a thermostated capillary compartment (5–50° C.) and a UV-Vis detector, Diode Array Detector (DAD) or Laser Induced Fluorescence (LIF) detector with a 3 mW Argon Laser module (488 nm) (Beckman Instruments Inc., Mississauga, Ontario) and a band pass filter 690±5 nm (i.d. 1 inch, ORIEL). Uncoated fused silica capillary columns were obtained from Polymicro Technologies (Phoenix, Ariz.). Unless otherwise specified, dimension were typically 50 $\mu$m i.d., 355 $\mu$m o.d. and 37 cm total length (30 cm to detector). The new capillary was treated with 1.0 M NaOH for 15 min followed by a 15 min rinse with deionized distilled water and equilibrated with the electrophoresis running buffer overnight before use. Data collection, processing and analysis were performed using the P/ACE™ Station software package (Beckman).

An AMINCO-Bowman series 2 luminescence spectrometer (SLM-AMINCO, Urbana, Ill.), a 8452A diode array spectrophotometer (Hewlett Packard), a 600E multisolvent delivery HPLC system with 991 photodiode array detector (division of Millipore, USA) were also used. Sep-Pak Cartridges were purchased from Waters (Milford, Mass., USA). A GLC-1 General Laboratory Centrifuge and Microfuge E™ (Beckman) and a Millex®-GV Filter Unit, 0.22 $\mu$m pore size (Millipore) were also employed.

Synthesis of BPD analogues

BPD-MA and BPD-DA (FIG. 1) were synthesized from the Diels-Alder adducts of protoporphyrin and dimethyl acetylene dicarboxylate (Richter et al. (1987)). The time of hydrolysis of the propionic dimethylesters with 25% hydrochloric acid dictates the final ratio between mono- and di-acids that are formed. The separation of the diacids from the monoacid analogues is achieved by chromatography (Richter et al. (1990)). Solutions of BPD-MA and BPD-DA were prepared in dimethyl sulfoxide (DMSO) at a concentration of 10 mg mL$^{-1}$. The stock solutions were stored frozen below 0° C. in the dark. Immnediately before use, a fraction of the stock solution was diluted with DMSO to a concentration of $2.0 \times 10^{-2}$ mg mL$^{-1}$.

Chemicals

Hydroxypropal-$\beta$-cyclodextrin (HP-$\beta$-CD), heptakis(2,6-di-O-methyl)-$\beta$-cyclodextrin (DM-$\beta$-CD), $\beta$-cyclodextrin (β-CD), and γ-cyclodextrin (γ-CD) were from Beckman Inc, Mississauga, Ontario and sodium dodecyl sulfate (SDS) from Fisher Inc. The structures of the chiral additives are shown in FIGS. 2A and 2B. Taurocholic acid, sodium salt hydrate, (+)-rutin hydrate, deoxycholic acid, sodium salt, monohydrate, glycyrrhizic acid, monoammonium salt hydrate, salicin and Brij 35 were obtained from Aldrich Chem. Co, Milw, Wis. Cholic acid, sodium salt, taurodeoxycholic acid, sodium salt, β-escin and rifamycin SV, sodium salt were purchased from Sigma (St. Louis, Mo., USA). The buffer stock solutions were pH 11.04, 100 mM 3-[cyclo-hexylamino]-n-propanesulfonic acid (CAPS); pH 9.2, 100 mM $Na_2B_4O_7$. $10H_2O$(Borax); pH 6.8, 100 mM ammonium acetate and pH 2.8, 100 mM citric acid (Sigma, St. Louis, Mo., USA). These were diluted to the appropriate concentration before use.

All solution were filtered through a 0.22 μm filter prior to use. Water was distilled and deionized with a NANO pure II ultra water system(Barnstead/Themolyne, Dubuque, Iowa, USA), DMSO, acetonitrile, 1-propanol, iso-propanol and methanol were HPLC grade (Fisher Scientific) and all other chemicals were of analytical grade and used without further purification.

Samples

Liposomally formulated benzoporphyrin derivative monoacid ring A (BPD-MA, Verteporfin) was provided by QLT PhotoTherapeutics Inc., Vancouver, Canada. Bovine serum and extracts from microsomes were liposomally formulated BPD-MA incubated with rat, dog and human and were provided by Dr. Julia Levy, Department of Microbiology, University of British Columbia, Vancouver, Canada.

Bovine Serum Preparation

The BPD-MA stock solution (1 mL, 0.1 mg $mL^{-1}$) was added to bovine serum (1.0 mL) or an acetone blank (1 mL), stirred well, and then acetonitrile (1.0 mL) was added. The mixture was stirred well and centrifuged (5 min at 2000 rpm). The supernatant was collected and the serum was re-suspended and washed twice in acetonitrile. The combined supernatants were filtered using a 0.22 μm filter. Recovery was determined using fluorescence detection. After evaporating the extracts to around 0.5 mL, the final volume was brought to 5.0 mL with water. The solution was then put into a Sep-Pak cartridge and washed with water. The Sep-Pak cartridge was rinsed with acetonitrile (5×1 mL). The eluates were evaporated, DMSO (200 μl) was added and the solution stirred and filtered using a 0.22 μm filter. The sample was then ready for CE separation.

EXAMPLE 2

CE Separation Procedures

The instrument was programmed to rinse the capillary at high pressure with 0.2 M NaOH for 5 min, pure water for 5 min. and then the separation buffer for 3 min. Samples were then introduced by a +10 KV electrokinetic injection for 2.0 sec. The separation was conducted in a constant-voltage mode by applying +20 KV across the ends of the capillary with normal polarity. The laser excitation wavelength was 488 nm and the fluorescence detection was monitored at 694 nm (10 nm, 1.0 inch band bass filter). The detector cell window was made by removing the polyimide coating on the capillary. The temperature of the capillary was held at 20° C. Data was collected at 5 Hz. Between runs, the capillary was cleaned and equilibrated with successive 5 min rinses of 1.0 M NaOH and pure water.

EXAMPLE 3

Separation of BPD-MA from its liposomal formulation

Into a 25 mL bottle containing liposomally formulated BPD-MA (25 mg) was added 12.5 mL of $H_2O$. After stirring, it was stored in the dark (below 0° C.) until use. A sample of this stock solution (5.0 μl) was added to DMSO (950 μl). The solution was stirred well and centrifuged for 5 minutes and filtered using a 0.22 μm solvent filter and then stored in the dark (4° C.) until use. 12.5 μl of this solution (2.0 mg $mL^{-1}$) was added to 25% acetonitrile/water and stirred well. The solution was then transferred into Sep-Pak cartridge and rinsed with 25% acetonitrile/water three times. The Sep-Pack was eluted with methanol (5×1.0 mL). The elutes were combined and evaporated under a nitrogen stream and the precipitate was dissolved in DMSO (5.0 mL), filtered using a 0.22 μm filter, and stored in the dark at 4° C.

All references cited hereinabove and below are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

References

Peng, X.; Bowser, M. T.; Britz-Mckibbin, P.; Bebault, G. M.; Morris, J. R.; Chen, D. D. Y. *Electrophoresis* 1997, 18, 706–716.

Delaney, T. F.; Glatstein, E. *Comprehensive Therapy* 1988, 14, 43.

Sternberg, E. D.; Dolphin, D. *Current Medicinal Chemistry* 1996, 3, 239–272.

Richter, A. M.; Kelly, B.; Chow, J.; Liu, D. J.; Towers, G. H. N.; Dolphin, D.; Levy, J. G. *J Natl. Can. Inst.* 1987, 79, 1327.

Jamieson, C. H. M.; McDonald, W. N.; Levy, J. G. *Leuk. Res.* 1990, 14, 209–219.

Neyndorff, H. D.; Bartel, D. L.; Tufaro, F.; Levy, J. G. *Transfusion* 1990, 30, 485–490.

Miller, H.; Miller, B. *Aich Opthalomol.* 1993, 111, 885.

Richter, A. M.; Waterfield, E.; Jian, A. K.; Allison, B.; Sternberg, E. D.; Dolphin, D.; Levy, J. G. *Br. J cancer* 1991, 63, 87–93.

Woodburn, K. W.; Stylli, S.; Hill, J. S.; Kaye, A. H.; Reiss, J. A.; Phillips, D. R. *Br. J VCancer* 1992, 65, 321–328.

Richter, A. M.; Sternberg, E. D.; Waterfield, E.; Dolphin, D.; Levy, J. G., *Proceeding SPIE*, the International Society for Optical Engineering, Boston, Mass. 1988, 997, 132–138.

Lim, C. K.; Li, F. M.; Peters, T. J. *Journal of Chromatography* 1988, 429, 123–53.

Wan, J. R.; Gouterman, M.; Green, E.; Khalil, G. *J. Liquid Chromatogr.* 1994, 17, 2045–2056.

Ho, J. W.; Candy, L. Y. F. *J. Liquid Chromatogr.* 1994, 17, 549–558.

Sato, H.; Ido, K. L.; Kimura, K. *Clin. Chem.* 1994, 40, 1239–1244.

Beukeveld, G. J. J.; Meerman, L.; Huizenga, J. R.; Venekamp-Hoolsema, E. E. A.; Gips, C. H.; Wolthers, B. G. *European J. Clin. Chem. & Clin. Biochem.* 1994, 32, 153–159.

Owens, J. W.; Robins, M.; Robinson, R.; Smith, R. *J. Chromatogr. B* 1996, 682, 327–336.

Richter, A. M.; Jain, A. K.; Canaan, A. J.; Waterfield, E.; Sternberg, E. D.; Levy, J. G. *Biochemical Pharmacology* 1992, 43, 2349–58.

Udagawa, M.; Hayashi, Y.; Hirayama, C. *Journal of Chromatography* 1982, 233, 338–42.

Kimmett, S. M.; Whitney, R. A.; Marks, G. S. Molecular Pharmacology 1992, 42, 307–10.

Walker, C. J.; Mansfield, K. E.; Rezzano, I. N.; Hanamoto, C. M.; Smith, K. M.; Castelfranco, P. A. *Biochemical Journal* 1988, 255, 685–92.

Hjerten, S. *Chromatogr. Rev.* 1967, 9, 122–219.

Jorgenson, J. W.; Lukacs, K. D. *Clin Chem* 1981, 27, 1551–3.

Kuhn, R.; Hoffstetter-Kuhn, S. *Capillary Electrophoresis Principles and Practice*; Springer-Verlag Berlin Heidelberg: Berlin, 1993.

Yao, Y. J.; Li, S. F. Y. *Journal of Liquid Chromatography & Related Technologies* 1996, 19, 1–15.

Weinberger, R.; Sapp, E.; Moring, S. *J Chromatogr* 1990, 516, 271–85.

Liu, X. H.; Xu, Y.; Ip, M. P. C. *Analytical Chemistry* 1995, 67, 3211–3218.

Bowser, M. T.; Sternberg, E. D.; Chen, D. D. Y. *Analytical Biochemistry* 1996, 241, 143–150.

Bowser, M. T.; Sternberg, E. D.; Chen, D. D. Y. *Electrophoresis* 1997, 18, 82–91.

Richter, A. M.; Cerruti-sola, S.; Sternberg, E. D.; Dolphin, D.; Levy, J. G. *J. Photochem. Photobiol.* 1990, 5, 231.

Wallingford, R. A.; Ewing, A. G. *J. Chromatogr.* 1988, 441, 299–309.

Pietta, P.; Mauri, P.; Bruno, A.; Gardana, C. *Electrophoresis* 1994, 15, 1326.

Morin, P.; Dreux, M.; Andre, P. *J. Chromatogr.* 1993, 628, 161–169.

Honda, S.; Makino, A.; Suzuki, S.; Kakehi, K. *Anal. Biochem.* 1990, 191, 228–234.

Honda, S.; Iwase, S.; Makino, A.; Fujiwara, S. *Anal. Biochem.* 1989, 176, 72–77.

Hoffstetter-Kuhn, S.; Paulus, A.; Gassmann, E.; Widmer, H. M. *Anal. Chem.* 1991, 63, 1541–1547.

Consden, R.; S., W. M. *Nature* 1952, 169, 783.

Boeseken, J. *Adv. Carbohydr. Chem.* 1949, 4, 189.

Landers, J. P.; Oda, R. P.; Schuchard, M. D. *Anal. Chem.* 1992, 64, 2846–2851.

Penn, S. G.; Bergstrom, E. T.; Goodall, D. M. *Anal Chem* 1994, 66, 2866–73.

Aveline, B. M.; Hasan, T.; Redmond, R. W. *J. Photochem. Photobiol. B Biology* 1995, 30, 161–165.

We claim:

1. A method of separating stereoisomers of benzoporphyrin derivatives (BPDs) with a capillary electrophoresis system, which method comprises:

selecting the capillary inner diameter, capillary length, field strength, separation temperature, pH, buffer system, ionic strength, chiral selector, and organic solvent of a capillary electrophoresis system to result in separation of BPD stereoisomers, injecting a sample containing said BPD stereoisomers into said capillary electrophoresis system, and separating said stereoisomers.

2. The method of claim 1 wherein said capillary electrophoresis system frther comprises a laser-induced fluorescence detection system.

3. The method of claim 1 wherein said BPDs are selected from BPD-MA, BPD-DA, and mixtures thereof.

4. The method of claim 1 or 2 wherein said separating results in baseline separation.

5. The method of claim 1, 2 or 3 wherein said capillary inner diameter is about 50 μm.

6. The method of claim 1, 2 or 3 wherein said capillary length is from about 27 to about 57 cm.

7. The method of claim 6 wherein said capillary length is about 37 cm.

8. The method of claim 1, 2 or 3 wherein said field strength is from about +15 to about +25 KV.

9. The method of claim 8 wherein said field strength is about +20 KV.

10. The method of claim 1, 2 or 3 wherein said separation temperature is from about 15 to about 30° C.

11. The method of claim 10 wherein said separation temperature is about 20° C.

12. The method of claim 1, 2 or 3 wherein said pH is from about 8.05 to about 9.6.

13. The method of claim 12 wherein said pH is from about 9.2.

14. The method of claim 1, 2 or 3 wherein said buffer system is borate.

15. The method of claim 1, 2 or 3 wherein said ionic strength is from about 200 to about 360 mM borate.

16. The method of claim 15 wherein said ionic strength is about 300 mM borate.

17. The method of claim 1, 2 or 3 wherein said chiral selector is a bile salt.

18. The method of claim 17 wherein said bile salt is a cholate salt.

19. The method of claim 18 wherein said cholate salt is sodium cholate.

20. The method of claim 1, 2 or 3 wherein said organic solvent is selected from the group consisting of DMF, isopropanol or acetonitrile.

21. The method of claim 20 wherein said organic solvent is acetonitrile.

* * * * *